United States Patent [19]    [11] Patent Number: 4,720,501
Binder et al.    [45] Date of Patent: Jan. 19, 1988

[54] 2-(2-THIENYL)-IMIDAZO(4,5-C)PYRIDINE DERIVATIVES AND SALTS THEREOF USEFUL IN THE TREATMENT OF MYOCARDIAL INSUFFICIENCY

[75] Inventors: Dieter Binder, Vienna; Franz Rovenszky, Bruck an der Leitha, both of Austria

[73] Assignee: Chemi Linz Aktiengesellschaft, Linz, Austria

[21] Appl. No.: 913,235

[22] Filed: Sep. 30, 1986

[30] Foreign Application Priority Data

Oct. 9, 1985 [AT] Austria ................. 2919/85

[51] Int. Cl.$^4$ ............... A61K 31/44; C07D 471/04
[52] U.S. Cl. .................. 514/303; 546/118
[58] Field of Search ............... 546/118; 514/303

[56] References Cited

U.S. PATENT DOCUMENTS 4,582,837  4/1986  Hauel et al. ............... 546/118
4,596,830  6/1986  Binder et al. ............... 546/118

Primary Examiner—Alan L. Rotman
Assistant Examiner—Bernard I. Dentz

[57] ABSTRACT

The invention relates to new 2-(2-thienyl)imidazo(4,5-c)pyridine derivatives of the formula

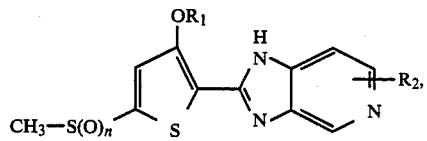

wherein $R_1$ denotes lower alkyl, $R_2$ denotes hydrogen or methyl and n denotes 0 or 1, and pharmaceutically usable acid addition salts thereof, a process for their preparation and pharmaceutical products containing these compounds. The new compounds and their salts have useful pharmacological properties, in particular a positively inotropic action on the heart, and can be used as active compounds for medicaments for the treatment of diseases of the heart and vessels, in particular myocardial insufficiency.

6 Claims, No Drawings

2-(2-THIENYL)-IMIDAZO(4,5-C)PYRIDINE DERIVATIVES AND SALTS THEREOF USEFUL IN THE TREATMENT OF MYOCARDIAL INSUFFICIENCY

The invention relates to new 2-(2-thienyl)imidazo(4,5-c)pyridine derivatives of the formula

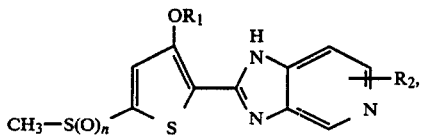

wherein $R_1$ denotes lower alkyl, $R_2$ denotes hydrogen or methyl and n denotes 0 or 1, and the pharmaceutically usable acid addition salts of compounds of the formula I, a process for their preparation, pharmaceutical products containing these compounds and their use in medicaments.

The expression "lower alkyl" used in this description means straight-chain or branched hydrocarbon radicals with 1 to 4 carbon atoms, such as, for example, methyl, ethyl, propyl, isopropyl, butyl, isobutyl, sec.-butyl or tert.-butyl.

In a preferred class of compounds of the formula I, $R_1$ denotes methyl or ethyl, and $R_2$ particularly preferably denotes methyl.

Particularly preferred individual compounds of the formula I are 2-(3-methoxy-5-methylthio-2-thienyl)-1H-imidazo(4,5-c)pyridine, 2-(3-methoxy-5-methylsulfinyl-2-thienyl)-1H-imidazo(4,5-c)pyridine and the hydrochlorides of these compounds.

The 2-(2-thienyl)-imidazo(4,5-c)pyridine derivatives of the formula I and salts thereof are preferably prepared, according to the invention, by methods which are known per se, by a process in which (a) a thiophenecarboxlyic acid derivative of the formula

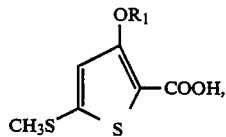

wherein $R_1$ has the meaning given in the case of formula I, or a salt thereof is converted into a thiophenecarboxylic acid chloride of the formula

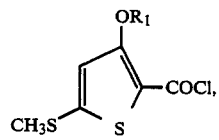

wherein $R_1$ has the meaning given in the case of formula I, by reaction with an inorganic acid chloride, this product is reacted with a diaminopyridine of the formula

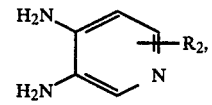

wherein $R_2$ is as defined in formula I, to give an isomer mixture consisting of the amides of the formula

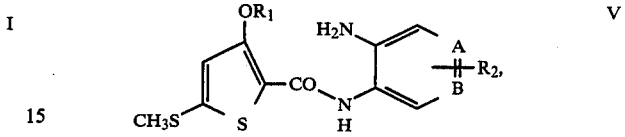

wherein $R_1$ and $R_2$ are as defined in formula I, one of the symbols A and B denotes the =N atom and the other in each case denotes a =CH ring member of the pyridine ring, the free bases in the resulting isomer mixture are converted into the hydrochlorides and these are cyclized with dehydrating agents to form the imidazole ring, after which (b) if appropriate, a resulting compound of the formula I wherein n denotes 0 is converted into a compound of the formula I in which n denotes the number 1 by treatment with organic peracids or hydrogen peroxide, and (c) if desired, a compound of the formula I obtained in process step (a) or (b) or a salt thereof which cannot be used pharmaceutically is converted into a pharmaceutically usable addition salt with inorganic or organic acids.

The preparation of the thiophenecarboxylic acid chlorides of the formula III in process step (a) is advantageously carried out by reaction of a thiophenecarboxylic acid of the formula II with an inorganic acid chloride, for example thionyl chloride, phosphorus oxychloride, phosphorus trichloride or phosphorus pentachloride, at low temperatures, the reaction with thionyl chloride at temperatures of about 0° C. being particularly preferred.

A thiophenecarboxylic acid chloride of the formula III obtained in the above reaction is subsequently reacted, according to the invention, with a 3,4-diaminopyridine of the formula IV under the reaction conditions customary for amide formation, an isomer mixture containing the amides represented by formula V being formed. The reaction of compounds of the formula III with those of the formula IV is advantageously carried out in a suitable organic solvent, preferably in pyridine, with the addition of a strong base, and the use of triethylamine has proved to be particularly advantageous for this purpose. For simplicity, the amides of the formula V can be prepared at room temperature, but temperatures which are just above or below room temperature are suitable, in the same manner per se, for the reaction.

The compounds of the formula V obtained in this reaction in the isomer mixture in the form of the free bases are converted into the hydrochloride before the cyclization, this conversion advantageously being effected by introducing HCl gas into a solution of the free bases in an inert organic solvent and subsequently precipitating the hydrochlorides, for example by addition of dry diethyl ether, and the hydrochlorides are then cyclized to compounds of the formula I wherein n denotes 0 in accordance with process step (a) by treatment with a dehydrating agent, the imidazole ring being formed.

The cyclization can also be carried out by direct treatment of the mixture of the hydrochlorides of the compounds of the formula V or advantageously by treatment of suspensions thereof in a suitable organic solvent or diluent, suspensions of the hydrochlorides in pyridine having provided to be particularly suitable. Possible dehydrating agents are the reagents usually employed for such cyclization reactions, for example phosphorus oxychloride, phosphorus pentachloride or thionyl chloride and the like.

The dehydrating reagent can be used for this purpose in equivalent amounts or, advantageously, in an excess, for example in amounts of 1.1 to 5 mol per mol of the mixture of the formula V. Slow addition of a 1.5- to 3-fold molar excess of phosphorus oxychloride to a suspension of the hydrochlorides of amides of the general formula V at room temperature or temperatures just above or below room temperature have proved to be a particularly advantageous cyclization method for the preparation of the compounds according to the invention.

According to process step (b), the sulfonyl compounds in which n in the formula I denotes the number 1 can be obtained by partial oxidation of the methylmercapto compounds of the formula I, where n denotes 0, obtained by process step (a), with suitable oxidizing agents. Oxidizing agents which are used are preferably approximately equivalent amounts of an organic peracid, such as peracetic acid, perbenzoic acid, m-chloroperbenzoic acid and the like, in a solvent which is inert in the reaction, for example methylene chloride or chloroform, advantageously at temperatures between $-5°$ C. and $-50°$ C., preferably at about $0°$ C., or approximately equivalent amounts of 30% strength hydrogen peroxide in glacial acetic acid, advantageously at room temperature.

The compounds of the formula I obtained by process step (a) or (b) have strongly basic properties. They can easily be converted into crystalline, pharmaceutically usable acid addition salts in the customary manner with inorganic or organic acids in accordance with process step (c), and the salts, such as, for example, the hydrochlorides, can readily be purified by recrystallization. For this, the crude base is advantageously dissolved in a suitable solvent, for example a lower aliphatic alcohol, an equivalent amount of the desired acid is added, the salts formed are precipitated or the solvent is evaporated off in vacuo and the residue is recrystallized from methanol or ethanol, if appropriate with the addition of ether or acetone.

Suitable examples of such pharmaceutically usable salts of compounds of the formula I are, in addition to the salt of hydrochloric acid, for example the salts of sulfuric acid, nitric acid, sulfonic acids, benzoic acid, maleic acid, tartaric acid and citric acid and of similar acids which have already been used for the preparation of pharmaceutically usable salts of known compounds.

The thiophenecarboxylic acid derivatives of the formula II used as starting materials for the process for the preparation of the compounds according to the invention are known from the literature (European Pat. No. A-0,148,742) or can be prepared in a manner which is known per se, starting from known compounds. The diaminopyridines of the formula IV are likewise known and, inter alia, are commercially available (for example from Fluka AG, Buchs, Switzerland).

The new compounds of the formula I and similarly their pharmaceutically usable acid addition salts exhibit extremely useful pharmacological properties both in vitro and in vivo in animal experiments. In particular, they have a strongly positive inotropic action on the heart and, as a result of their cardiotonic properties, they can therefore be used in human medicine for the treatment and prophylaxis of diseases of the heart and vessels, in particular for the treatment of myocardial insufficiency and pathological consecutive symptoms thereof.

To ascertain these pharmacological properties, compounds according to the invention were subjected to the following generally recognized pharmacological investigations:

(1) Positively inotropic action on the isolated guineapig auricle

The action of compounds of the formula I on the frequency and contraction force of freshly prepared isolated guinea-pig auricles was tested. For this, the test substances were investigated in concentrations in the range from $10^{-7}$ to $3.10^{-4}$ mol/l, the auricles of untreated animals being used in a first series of experiments and those of animals treated with reserpine being used in a second series of experiments.

Result:

In this standard text, compounds according to the invention had the effect of a significant dosedependent increase in the contraction force of isolated, electrically stimulated, left auricles from guinea pigs. For example, the compound of the formula I, 2-(3-methoxy-5-methylsulfinyl-2-thienyl)-1H-imidazo(4,5-c)pyridine hydrochloride, effects a 50% of increase in the contraction force at a concentration $1.2 \times 10^{-4}$ mol/l. The effect on the contraction force is thus qualitatively comparable to that of the known cardiac glycoside quabaine, that is to say 3-((6-deoxy-alpha-L-mannopyranosyl)oxy)1,5,11 alpha, 14,19-pentahydroxy-card-20(22)-enolide.

In comparison with quabaine, the compounds according to the invention, such as 2-(3-methoxy-5-methylsulfinyl-2-thienyl)-1H-imidazo(4,5-c)pyridine hydrochloride, have the advantage that even in the upper concentration range investigated, no therapeutically undesirable increase in rate occurs on the spontaneously beating right auricle from guinea pigs.

Pretreatment with reserpine only slightly impairs the action of the substances investigated, so that a direct action mechanism can be assumed for the compounds according to the invention. Compounds of the formula I accordingly exhibit a clear, direct positively inotropic action, coupled with only a very weak positively chronotropic action, on the isolated auricle of guinea pigs.

(B) Investigations on anesthetized dogs

Compounds according to the invention were injected in doses of 3 to 3,000 ug/kg cumulatively into the v. jugularis of beagle dogs anesthetized with alpha chloralose (1,2-0-(2,2,2-trichloroethylidene)-alpha-D-glucofuranose). After the administration, the action on the left ventricular pressure (LV dp/dt), the fermoralis pressure and flow, the cardiac output (CO) and the heart rate was investigated.

Result:

In these investigations, the compounds according to the invention effect on the one hand a significant dose-dependent increase in the left ventricular pressure and the cardiac output, and on the other hand a decrease in the left ventricular end diastolic pressure and the peripheral diastolic blood pressure.

Thus, for example, 2-(3-methoxy-5-methylsulfinyl-2-thienyl)-1H-imidazo(4,5-c)pyridine hydrochloride already leads to a marked increase in the left ventricular pressure (LV dp/dt = +113%), without an undesirable influence on the heart rate, at a dose of 300 ug/kg. At this dose, the substance exhibits a significant, strongly positively inotropic action on anesthetized dogs. A clear increase in heart rate occurs only at doses of 1 to 3 mg/kg intravenously, which are far outside the therapeutic use range.

Cardiac glycosides or sympathomimetic amines have to date been administered as substances with a positively inotropic action. Cardiac glycosides caused side effects, such as dangerous cardiac disrhythmia, in many cases and must be used with care, because of their high toxicity. Sympathomimetic amines have only limited possible uses, inter alia because of their positively chronotropic side effect, arhythomgenic properties and oral ineffectiveness. Because of their pronounced and at the same time very specific positively inotropic action, the substances according to the invention thus respresent an interesting class of new active compounds which could replace, with great advantage to the patient, the products previously used for the treatment of myocardial insufficiently.

On the basis of their favorable properties, the compounds of the formula I and salts thereof can be used as medicines, for example in the form of pharmaceutical products which contain the compounds according to the invention mixed with a pharmaceutical, organic or inorganic excipient suitable for enteral or parenteral administration, for example water, gelatine, gum arabic, lactose, starch, magnesium stearate, talc, vegetable oils, vegetable or animal fats, polyalkylene glycols, vaseline and the like. The pharmaceutical products can be in solid form, for example in the form of tablets, coated tablets, suppositories or capsules, or in liquid form, for example in the form of solutions, suspensions or emulsions. If appropriate, they are sterilized and/or contain auxiliaries, such as preservatives, stabilizers or emulsifying agents and salts for modifying the osmotic pressure. In particular, they can also be administered in combination with other therapeutically useful substances.

The following examples illustrate the invention in more detail:

EXAMPLE 1

2-(3-methoxy-5-methylthio-2-thienyl)-1H-imidazo(4,5-c)-pyridine 4.0 g (19.6 mmol) of 3-methoxy-5-methylthio-2-thiophenecarboxylic acid are stirred into 40 ml of $SOCl_2$ at 0° C., the mixture is stirred for 20 minutes and the excess solvent is evaporated off at room temperature in vacuo.

The crude acid chloride (4.3 g, melting point =98°-101° C., diisopropyl ether) is dissolved in 25 ml of dry benzene and the solution is added dropwise to a mixture of 2.1 g (19.6 mmol) of 3,4-diaminopyridine, 14 ml of absolute pyridine and 10 ml of triethylamine at 20° C. in the course of 10 minutes. The mixtures is stirred at room temperature for a further 90 minutes. The reaction mixture is largely evaporated, the residue is diluted with 50 ml of water and the mixture is acidified to pH 4 with 2 N HCl, brought to pH 7 with $NaHCO_3$ and extracted three times with a total of 200 ml of ethyl acetate. The combined organic phases are dried over sodium sulfate and filtered and the filtrate is concentrated to 50 ml. HCl gas is passed at a temperature of less than 30° C. into the solution which remains, until this is saturated, and 250 ml of dry diethyl ether are then added. The oil which has separated out is decanted and is washed twice more with 100 ml of dry ether each time and freed from residual ether in vacuo.

The mixture of the amides is suspended in 50 ml of absolute pyridine, and 5.76 g (37.6 mmol) of $POCl_3$ are added dropwise at 20° C. in the course of 5 minutes, with stirring. The mixture is stirred at room temperature for a further 90 minutes. It is then largely evaporated and the residue is partitioned between 50 ml of saturated $NaHCO_3$ solution and 50 ml of ethyl acetate. The aqueous phase is extracted twice more with 40 ml of ethyl acetate each time and the combined organic phases are dried over sodium sulfate and evaporated. The residue (2.8 g) is taken up in 150 ml of methanol, excess methanolic hydrochloric acid is added, the mixture is filtered hot, after addition of active charcoal, the solution is concentrated to about 50 ml and cooled and the yellow hydrochloride which has precipitated out is filtered out with suction, washed with a little cold methanol and dried in vacuo (1.6 g).

To prepare the free base, 1.6 g (5.10 mmol) of the hydrochloride are suspended in 12 ml of methanol, excess aqueous ammonia is added and the product is precipitated by addition of 40 ml of water. It is filtered off with suction, washed with water and dried at 60° C./20 mbar.

Yield: 1.27 g

Melting point=165°-167° C. (2-butanone/Et$_2$O=3:1).

EXAMPLE 2

2-(3-methoxy-5-methylsulfinyl-2-thienyl)-1H-imidazo(4,5-c)pyridine 0.50 g (1.80 mmol) of 2-(3-methoxy-5-methylthio-2-thienyl)-1H-imidazo(4,5-c)pyridine is dissolved in 30 ml of chloroform, the solution is cooled to −10° C. and a solution of 0.40 g (1.98 mmol) of 85% strength 3-chloroperbenzoic acid in 10 ml of chloroform is added dropwise at this temperature in the course of 10 minutes, with stirring. The mixture is stirred at −10° C. for a further 10 minutes and extracted twice with 8 ml of saturated $NaHCO_3$ solution each time and the organic phase is dried over sodium sulfate and evaporated.

Yield: 0.46 g (87%)

Melting point=235° C. (methanol)

EXAMPLE 3

2-(3-methoxy-5-methylthio-2-thienyl)-1H-imidazo(4,5-c)-pyridine hydrochloride 1.0 g (3.6 mmol) of 2-(3-methoxy-5-methylthio-2-thienyl)-1H-imidazo-(4,5-c)pyridine are suspended in 25 ml of methanol, and 7 ml of 1 N methanolic HCl are aded. The mixture is evaporated to dryness in vacuo and the residue is recrystallized from methanol.

Yield: 1.04 g (92%)

Melting point=234°-236° C. (decomposition; methanol)

EXAMPLE 4

2-(3-methoxy-5-methylsulfinyl-2-thienyl)-1H-imidazo-(4,5-c)pyridine hydrochloride 0.4 g (1.36 mmol) of 2-(3-methoxy-5-methylsulfinyl-2-thienyl)-1H-imidazo(4,5-c)pyridine is suspended in 13 ml of methanol, and 3 ml of 1 N methanolic HCl are added. The mixture is evaporated to dryness and the residue is recrystallized from methanol/acetone.

Yield: 0.37 g (83%)
Melting point=204°-207° C. (methanol/acetone)
What we claim is:

1. A 2-(2-thienyl)-imidazo(4,5-c)pyridine derivative of the formula

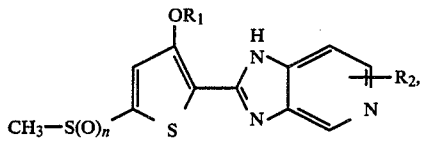

wherein $R_1$ denotes lower alkyl, $R_2$ denotes hydrogen or methyl and n denotes 0 or 1, or a pharmaceutically usable acid addition salt thereof of a compound of the formula I.

2. The compound of the formula I as defined in claim 1, wherein $R_1$ denotes methyl or ethyl.

3. The compound as claimed in claim 1, which is 2-(3-methoxy-5-methylthio-2-thienyl)-1H-imidazo(4,5-c)pyridine and the hydrochloride thereof.

4. The compounds as claimed in claim 1, which is 2-(3-methoxy-5-methylsulfinyl-2-thienyl)-1H-imidazo(4,5-c)pyridine and the hydrochloride thereof.

5. A pharmaceutical composition comprising a compound of formula I or an acid addition salt thereof as claimed in claim 1 in an amount effective for the treatment of congestive heart failure in combination with a pharmaceutically acceptable carrier or diluent.

6. A method for the treatment of congestive heart failure which comprises administering an effective amount of a compound of formula I or an acid addition salt thereof as claimed in claim 1 to a patient suffering from congestive heart failure.

* * * * *